US005626711A

United States Patent [19]
Herrmann

[11] Patent Number: 5,626,711
[45] Date of Patent: May 6, 1997

[54] APPARATUS FOR PRODUCING ELASTICIZED UNDERGARMENT PRODUCTS

[75] Inventor: Thomas R. Herrmann, Federal Way, Wash.

[73] Assignee: Paragon Trade Brands, Inc., Norcross, Ga.

[21] Appl. No.: 250,289

[22] Filed: May 27, 1994

[51] Int. Cl.⁶ ................................................. A61F 13/15
[52] U.S. Cl. .......................... 156/496; 156/163; 156/164; 156/229; 156/269; 156/495; 156/538
[58] Field of Search ................................. 156/163, 164, 156/229, 494, 495, 496, 538, 539, 250, 269; 271/226, 229

[56] References Cited

U.S. PATENT DOCUMENTS

| 2,423,294 | 7/1947 | Colesworthy | 156/496 X |
|---|---|---|---|
| 3,531,347 | 9/1970 | Stultz, Jr. | 156/494 X |
| 3,644,157 | 2/1972 | Draper | 156/160 |
| 4,284,454 | 8/1981 | Joa | 156/164 X |
| 4,492,608 | 1/1985 | Hirsch et al. | |
| 4,585,507 | 4/1986 | Bradley et al. | |
| 4,765,854 | 8/1988 | McKeown | |
| 4,941,939 | 7/1990 | Nomura et al. | |
| 4,968,313 | 11/1990 | Sabee | 156/164 X |
| 5,190,606 | 3/1993 | Merkatoris et al. | |
| 5,389,173 | 2/1995 | Merkatoris et al. | 156/495 X |
| 5,411,618 | 5/1995 | Jocewicz, Jr. | 156/229 X |

*Primary Examiner*—Jeff H. Aftergut
*Attorney, Agent, or Firm*—Klarquist Sparkman Campbell Leigh & Whinston, LLP

[57] ABSTRACT

Apparatus and method for producing a product, such as a disposable absorbent garment, from flexible material having elasticized portions tending to contract the product as it moves along a path. The apparatus includes a plurality of spaced apart engaging members which grip opposed edge and end margins of the product and a conveyor on which the engaging members are mounted to carry the engaging member and products stretched therebetween along a production path. At various stations along the production path apparatus is provided for retarding forward movement of one of the sets of engaging members to fold a leading edge portion thereof back into a position overlying a trailing end portion thereof, joining, or sealing, apparatus for sealing side edge margins together, and severing mechanism for severing the article from the engaging members. A holding rod extends longitudinally and is received within the garment as it is folded over to hold it in a laterally stretched condition after it is released from the engaging members. A tucking member downstream from the severing mechanisms is operable to tuck in side edge margins to produce a properly folded garment ready for packaging.

12 Claims, 6 Drawing Sheets

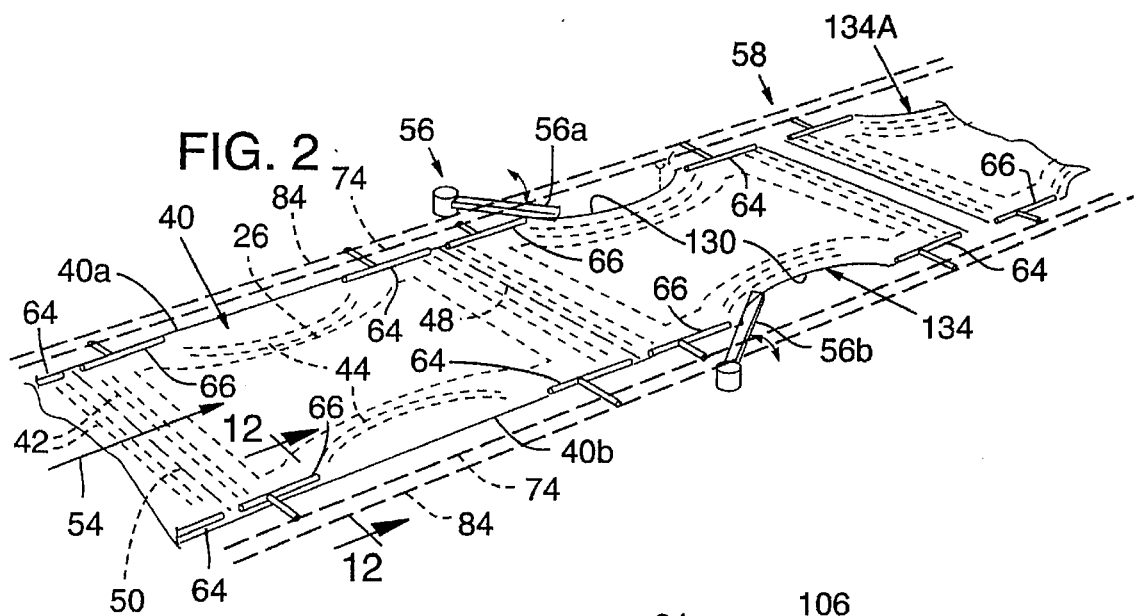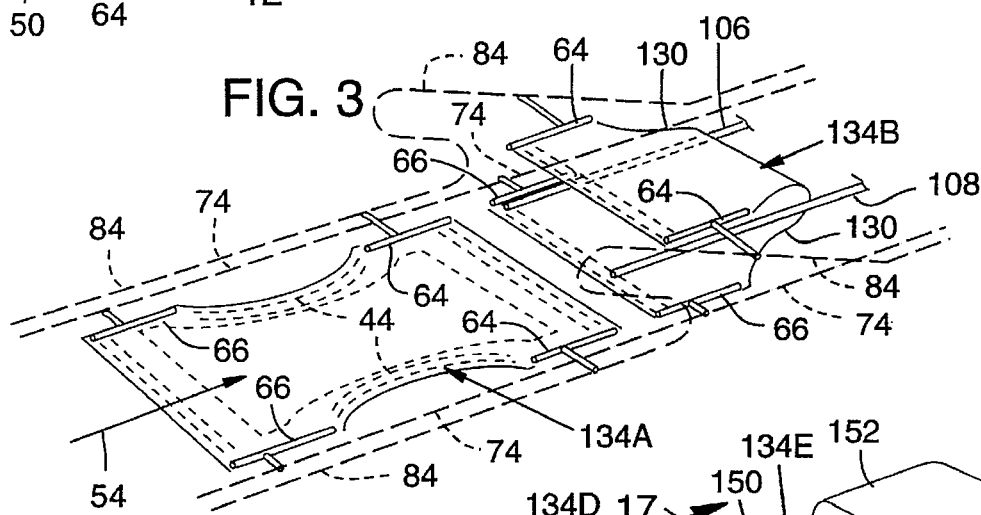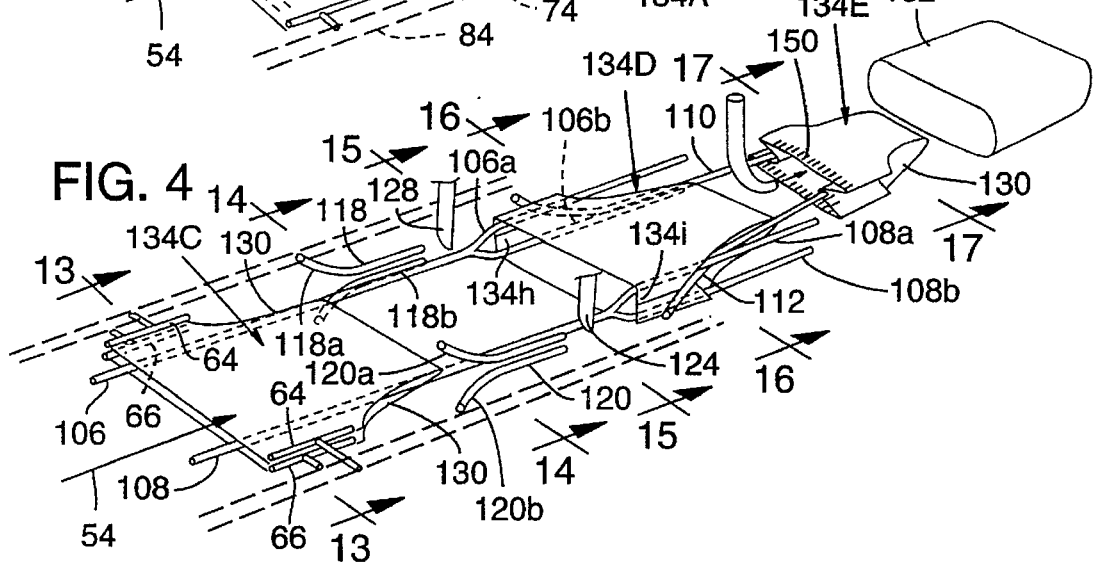

APPARATUS FOR PRODUCING ELASTICIZED UNDERGARMENT PRODUCTS

BACKGROUND OF THE INVENTION

This invention relates to apparatus and method for producing products composed of flexible sheet material having elastic portions tending to contract the product during manufacture, and more particularly to apparatus and method which maintains the sheet material in stretched condition during assembly and produces appropriate folding, sealing, tucking and other desired operations thereon.

In the production of products manufactured of flexible sheet material, such as in the manufacture of disposable absorbent garments, it is often difficult to control the orientation of the flexible sheet material as it moves through the manufacturing process. In many instances, it is necessary to maintain the sheet material substantially planar while various operations are exercised upon it.

This difficulty in maintaining control of the sheet material becomes even more pronounced when elastic members are a part of the product. For example, in the production of disposable absorbent garments such as diapers or training pants, elastic members are secured to the sheets extending transversely thereof to provide fitted waistbands, and longitudinally extending elastic elements are attached to provide form-fitting leg cuffs in the garment.

In the past it has been difficult to maintain such products in a stretched substantially planar orientation as the products are carried along a path during the manufacturing operation due to the tendency of the elastics to contract the product. Further, problems have existed in holding the sheet material and product in proper orientation during operations to produce needed folding, joining, trimming with movement of the product along a conveying path to produce a finished product.

SUMMARY OF THE INVENTION

A general object of the present invention is to provide novel apparatus and method for maintaining longitudinally and laterally stretched conditions for such products as they are moved along a path during manufacture.

More specifically, an object is to provide engaging members which hold opposed end and side regions of a product in a defined stretched condition and carry the product along a desired manufacturing path during operation.

A further object is to provide novel apparatus and method in which such a product may be folded over about a central region thereof whereby a leading portion may be laid over a trailing portion to define a folded over product as desired.

Yet another object is to provide novel apparatus which provides continued holding of marginal edge portions of such a product while it is folded over and then joins portions thereof to provide a substantially continuous waistband portion for a garment, which then is severed from the engaging and holding mechanism.

A further object of the present invention is to provide novel apparatus and method for producing inwardly defined tucks in selected regions of a product produced in accordance with the invention prior to final packaging.

The above and other objects of the invention are accomplished by providing apparatus for producing a product of flexible material having elasticized portions tending to contract the product as it is moved along a path, which apparatus includes a plurality of spaced-apart engaging members operable to engage and hold the product adjacent opposed end regions and opposed side regions thereof and a conveyor operable to maintain selected spacing between the engaging members to maintain the product stretched both longitudinally and laterally and to carry the engaging members along the path for the product at a selected speed while maintaining the selected spacing.

The engaging members may include four members, each positioned to engage the product adjacent an intersection between an end region and a side region thereof, with the engaging members spaced apart to maintain the product stretched longitudinally and laterally. The conveyor may include a first pair of conveyor elements carrying a first pair of opposed engaging members positioned to engage opposed side edge margins of the product adjacent a leading portion of the product, and a second pair of conveyor elements disposed adjacent and extending along opposite side margins of the path which carry a second pair of opposed engaging members spaced longitudinally of the path from the first pair of engaging members to engage opposed side margins of the product adjacent a trailing portion thereof.

In another embodiment of the present invention turning mechanism is provided which is operable to cause the first engaging members to pivot as they are moved along the path to fold a leading portion of the product over a trailing portion thereof. The turning mechanism is operable to retard movement of the first conveyor elements longitudinally of the path, relative to the second conveyor elements in the region of the turning, to place the leading portion of the product in registry with the trailing portion.

In a further embodiment of the invention, a tucking member is provided to engage and tuck a portion of the product laterally inwardly into a fold.

The invention further includes a method for producing an absorbent garment including the steps of overlaying first and second elongate webs of flexible sheet material, with absorbent pad material interposed and encased therebetween, and applying elastic material thereto extending laterally and longitudinally to form an elongate composite having sections adapted to be separated therefrom to form discrete products, each having opposed end regions and opposed side regions. The method further includes providing spaced-apart engaging members carried by a conveyor, engaging and holding the composite adjacent portions thereof which define opposed end regions and opposed side regions of a discrete product in the composite, and maintaining selected spacing to maintain the product stretched, both longitudinally and laterally while the product is moved along the path.

Further, a method is provided wherein a leading end portion of the product is folded back over a trailing end portion thereof to place the leading end portion in registry with the trailing end portion.

These and other objects and advantages will become more fully apparent as the following description is read in conjunction with the drawings.

DRAWINGS

FIG. 2 is an enlarged perspective view of a portion of the apparatus and an exemplary illustration of a portion of the method for forming products in the apparatus of FIG. 1;

FIG. 3 is an extension of the assembly apparatus and process following that illustrated in FIG. 2;

FIG. 4 is an extension of the assembly apparatus and process following that illustrated in FIG. 3;

FIGS. 12, 13, 14, 15, 16 and 17 are schematic illustrations taken generally along the lines 12—12, 13—13, 14—14, 15—15, 16—16, and 17—17 in FIGS. 2, 3, and 4, respectively.

DETAILED DESCRIPTION OF PREFERRED EMBODIMENT OF THE INVENTION

Figure 1:
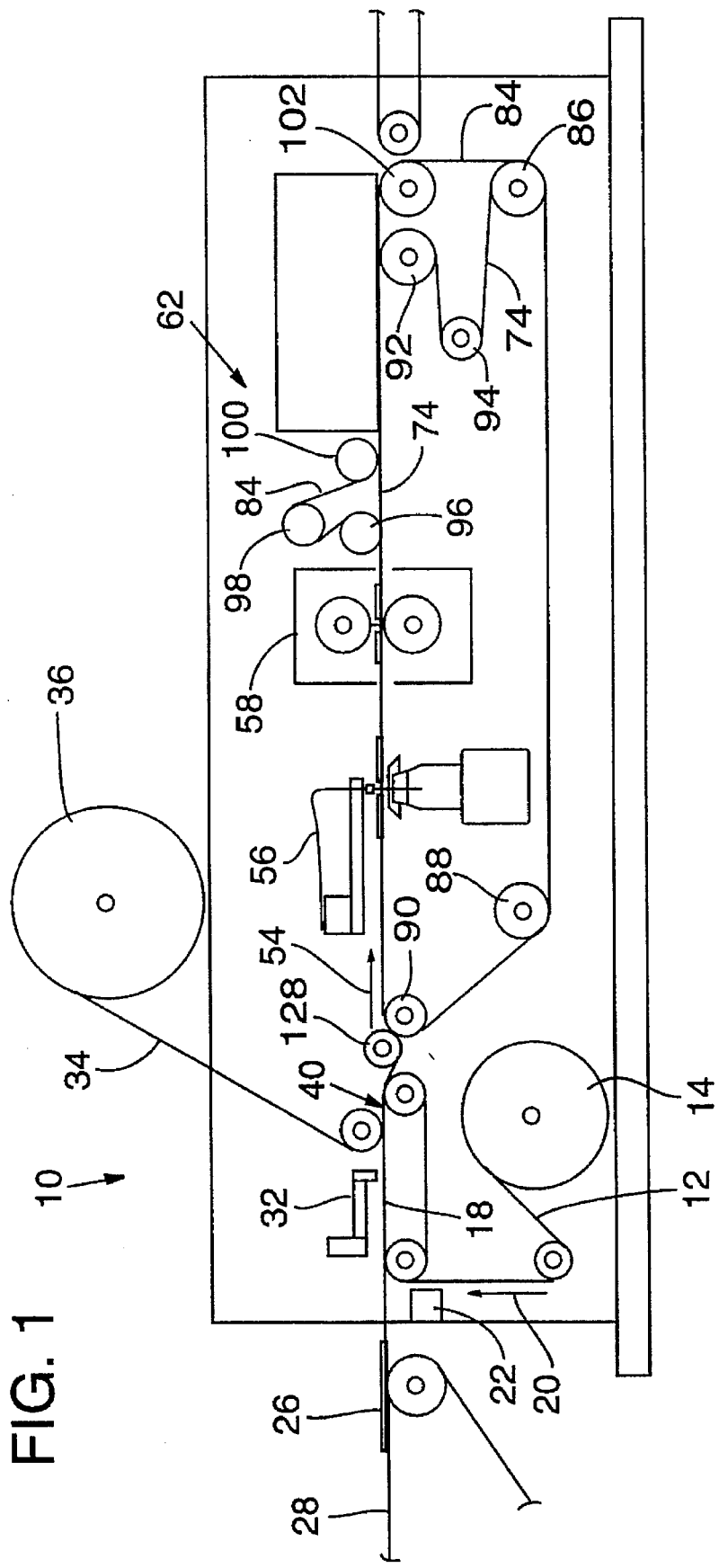
FIG. 1 is a schematic side elevation view of apparatus according to an embodiment of the present invention for producing articles, such as disposable absorbent garments including training pants.

Referring first to FIG. 1 at 10 is indicated generally apparatus constructed according to an embodiment of the invention. The apparatus is illustrated specifically in use to produce disposable diapers or training pants, but it should be understood that it is not limited to such products.

As is known, disposable diapers and training pants generally include an outer, or backing, sheet of a liquid impervious material, onto which an absorbent pad is placed. A liquid pervious liner, or inner, sheet is placed thereon to encase the absorbent pad therebetween. One such garment and method of manufacture is illustrated in U.S. Pat. No. 4,726,807 to Young and Lancaster, which is herein incorporated by reference to illustrate typical material used and known methods of manufacturing such garments.

In the manufacture of such products it often is desirable to provide strands, or bands, of elastic material extending transversely of the inner and outer sheets to produce elasticized waist areas for the garment and longitudinally extending elastic to form leg cuffs. Such products often are manufactured on assembly lines in which the garment material moves substantially continuously longitudinally, in what is referred to as the "machine direction". The elastic tends to cause the sheet material to contract both laterally and longitudinally which produces difficulties in the manufacturing process.

An elongate sheet, or web, of flexible liquid-impervious backsheet material 12 is carried from a roll 14 upwardly along a path denoted at 20 and onto a conveyor 18. As it is carried upwardly laterally extending elongate waist elastic elements are applied thereto by a waist elastic applicator indicated schematically at 22. Apparatus for applying waist elastic are known in the art and thus will not be described in detail here.

An elongate absorbent pad 26 is carried by a conveyor 28 and deposited on backsheet 12. A plurality of elongate leg elastic elements are applied to the backsheet in desired curvilinear pattern extending substantially longitudinally of the backsheet by a leg elastic applicator indicated schematically at 32. Leg elastic applicators also are known in the art and thus will not be described in detail here. An elongate web, or sheet, of liquid-pervious material to form an inner liner, or top sheet 34 is drawn from a roll 36 and deposited on pad 26 and backsheet 12 to encase the absorbent pad therebetween.

For example, the liquid impervious backsheet 12 may be a thin thermoplastic material, such as a pigmented polyethylene film having a thickness in the range of 0.02–0.04 mm. The liquid pervious liner sheet 16 may be a carded polyester fiber with a latex binder or a spun-bonded polypropylene having continuous fibers and thermally bonded by patterned calendar rolls. The liner sheet may be impregnated with a surfactant to render it hydrophilic. The moisture absorbent layer, or pad, 26 may be of wood fibers or other fibers, such as chemical wood pulp, or any other suitable liquid absorbing material such as commercially available fluff pulp or a fluffed bleached craft soft wood pulp.

These elements are secured together by adhesive or heat bonding to define an elongate composite product indicated generally at 40 in FIG. 2. The composite has a backsheet 12 and topsheet 34 encasing a pad 26 therebetween. In FIG. 2 transversely extending waist elastics are indicated generally in dashed line at 42 and leg elastics extending in curvilinear patterns, but generally longitudinally thereof are indicated as dashed lines at 44. A pair of spaced, laterally extending dashed lines 48, 50 define separation regions between discrete products to be formed in the manufacturing process from the elongate composite thus far described. Apparatus and methods for forming a composite as thus far described is generally known in the art. Since the composite thus formed includes laterally and longitudinally extending elastic elements 42, 44 it has a tendency to contract both laterally and longitudinally. The apparatus of the present invention is operable to hold the flexible elasticized materials in a substantially stretched and planar condition for handling in the operations to be described below.

Referring still to FIG. 1, various operational stations are indicated only schematically. As the composite product 40 is carried longitudinally along a path indicated generally at 54, in what is termed the machine direction, spaced side margin regions thereof are incut to form what will become leg portions for the garment. These cuts are made by water jets indicated generally at 56. Discrete products will be separated from the composite at separation lines, such as those indicated generally at 48, 50, by a final knife section noted at 58. The discrete products then will be carried through what is referred to as a fold, seal and trim region indicated generally at 62.

Referring to FIGS. 2, 3, and 4, the apparatus in the fold, seal and trim unit is illustrated generally in perspective view. FIG. 3 is a longitudinal extension of the end of FIG. 2, and FIG. 4 is a longitudinal extension of the end of FIG. 3. In actuality, no break would occur between the elements shown in FIGS. 2, 3, and 4 and they would form a common direct extension, one of the other.

Referring to FIG. 2, a pair of laterally spaced first engaging, or gripping, members 64 are positioned to grip, or hold, opposed side edge margins, or portions of what will be referred to herein as a leading end portion, or region, of a garment, or product, adjacent separation line 48. A pair of second engaging, or gripping, members 66, which also are spaced laterally of the path of the garment, are positioned to engage, or grip, what is referred to herein as a trailing end portion of a product, or garment, adjacent separation line 50. These engaging members, as will be described in greater detail below, are operable to grip, or hold, opposite end portions and opposite side portions of the product and maintain the product stretched both longitudinally and laterally against the contracting tendencies of elastics 42, 44, thus to hold the product in substantially planar condition as it is carried longitudinally along path 54 in the apparatus.

Figure 8:
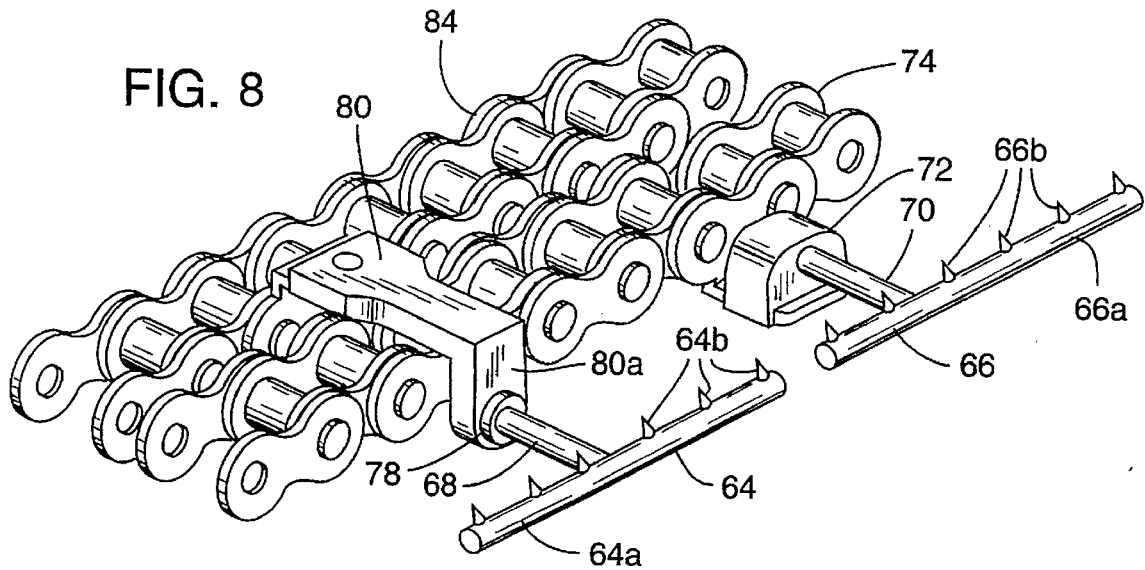
FIG. 8 is an enlarged perspective view of a portion of the conveyor and product engaging members in the apparatus with two engaging members being substantially co-extensive, and spaced apart longitudinally of the apparatus.
Figure 12:
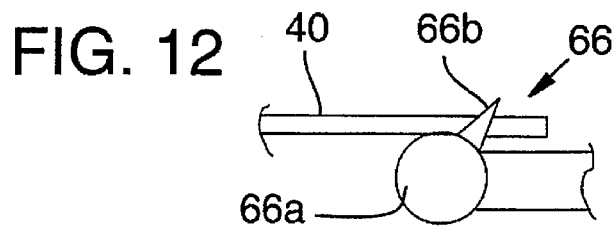
Figure 13:
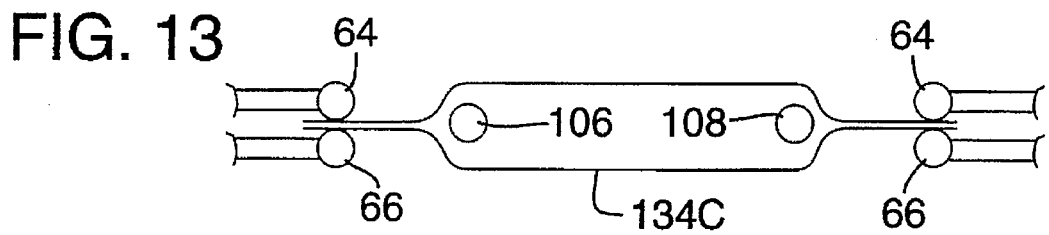

Referring to FIGS. 8 and 12, it will be seen that engaging members 64, 66 include elongate bars 64a, 66a which have pins or teeth, 64b, 66b projecting upwardly therefrom. The teeth are angled somewhat laterally outwardly from the center of the conveyor path. An elongate connecting rod 68 is secured to and extends perpendicularly from the center of bar 64a, and a connecting rod 70 is secured to and extends substantially perpendicularly outwardly from rod 66a in a region offset from the center of rod 66a. A substantially rigid connector block 72 connects engaging member 66 to an elongate endless conveyor chain 74. Connecting rod 68 is rotatably connected through a pivot connection 78 to a downwardly depending leg 80a of an angle bracket 80. The opposite end of bracket 80 is secured to and movable with an elongate endless conveyor chain 84.

Figure 7:
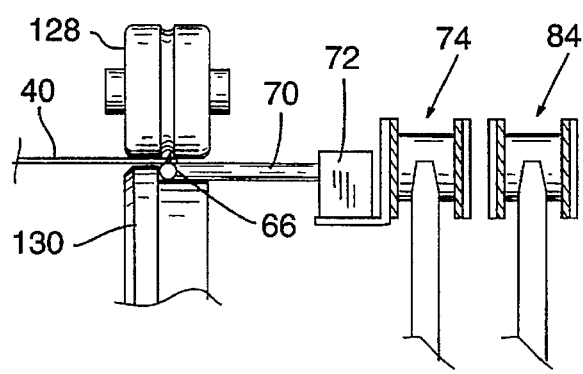
FIG. 7 is an enlarged cross-sectional view taken generally along the lines 7—7 in FIG. 5.

In FIGS. 7 and 12 an engaging member 66 is illustrated positioned with an edge margin portion of composite product 40 impaled on pins 66 for carrying the flexible sheet materials in substantially planar condition along the path of the apparatus. Engaging members 64 similarly hold side, or edge, margin portions of the composite product 40.

Figure 9:
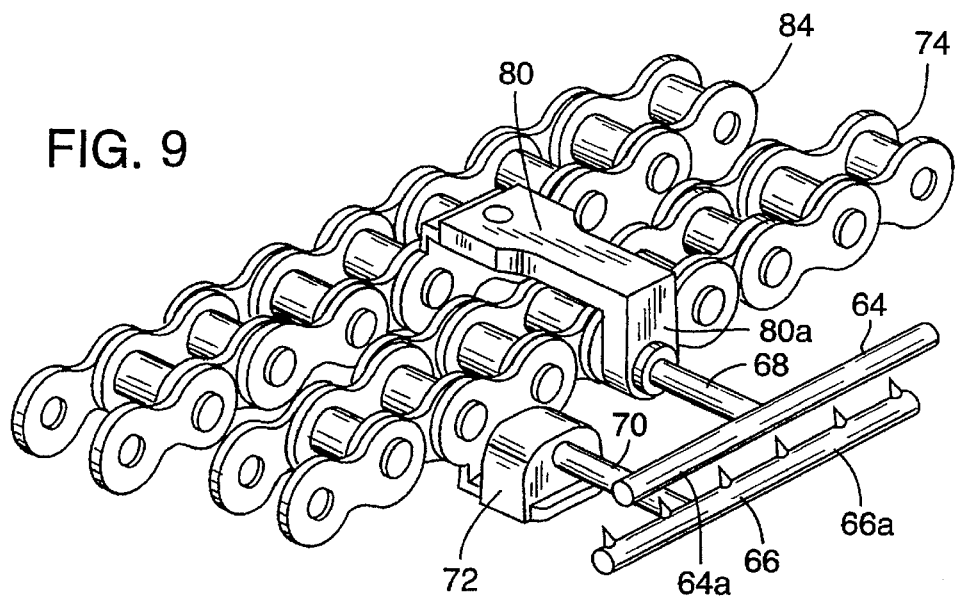
FIG. 9 is a view similar to FIG. 8, but with one of the engaging members inverted and overlying the other engaging member.
Figure 10:
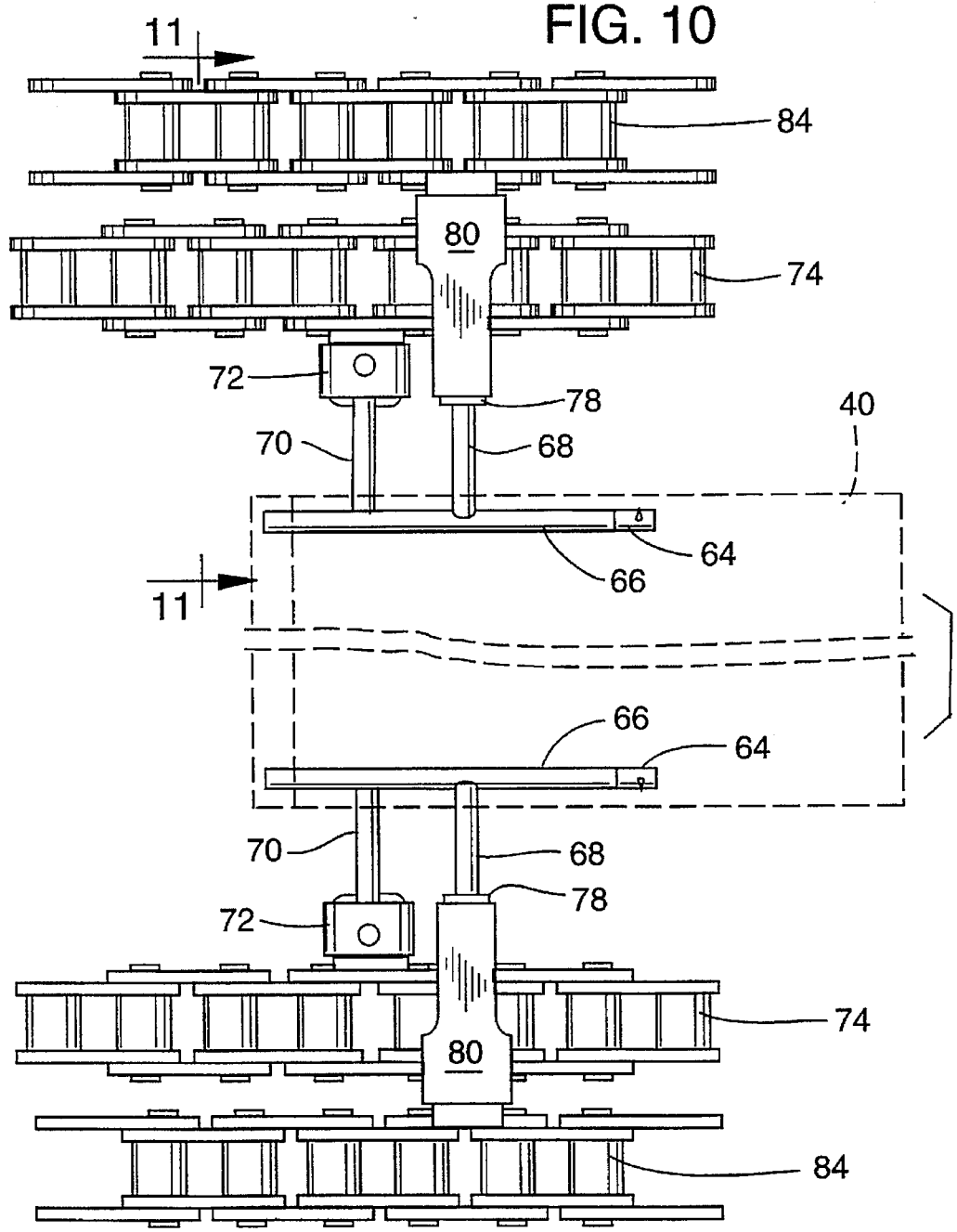
FIG. 10 is a top plan view of the conveyors and engaging members holding a work piece therebetween when positioned as illustrated in FIG. 9.
Figure 11:
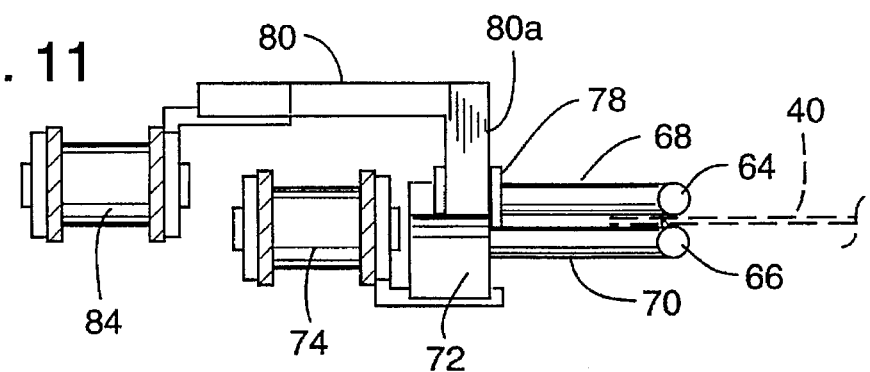
FIG. 11 is a view taken generally along the line 11—11 in FIG. 10.

FIGS. 9–11 illustrate engaging members 64, 66 positioned as they will lie upon folding over a product in the assembly process. This will be described in greater detail below.

Figure 5:
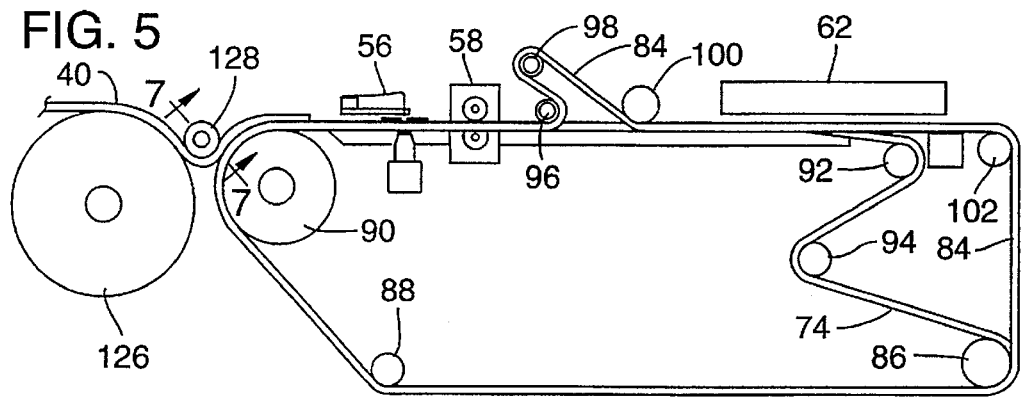
FIG. 5 is a schematic side elevation view of a portion of conveyor mechanism operable to carry product through the assembly apparatus.

Referring to FIG. 5, the general paths for conveyor chains 74, 84 are illustrated. The apparatus includes conveyor chains 74, 84 at opposite sides of the product path as seen in FIGS. 2–4 and 10. Both conveyor chains 74, 84 at opposite sides of the apparatus are trained around sprockets positioned as generally indicated at 86, 88, and 90. As they travel along the upper portion of the conveyor run chain 74 maintains a substantially horizontal run from sprocket 90 to sprocket 92. It then makes a reverse bend around sprocket 94 and then back to a sprocket positioned as generally noted at 86.

Chain 84, on the other hand, travels from sprocket 90, about sprocket 96, upwardly and rearwardly about sprocket 98, and then inclines downwardly and forwardly along the conveyor path under sprocket 100 to then make a turn downwardly at sprocket 102. The reverse curvatures of the conveyor paths for chains 74 and 84 is such that they will maintain their desired spacing and action as they move along the upper reach of the conveyor apparatus as will be described below.

Referring again to FIGS. 3 and 4, a pair of laterally spaced, longitudinally extending, horizontal elongate holding rods, or elements, 106, 108 are mounted to extend into the region between the elevations of sprockets 98 and 100 and are spaced laterally inwardly toward the center of the product path from engaging members 64, 66. Mounting and support structure for holding elements 106, 108 is omitted for clarity in the drawings.

Adjacent the downstream ends of rods 106, 108 they are bifurcated into horizontally disposed, vertically spaced elongate, upper and lower legs 106a, 106b and 108a, 108b, respectively A pair of substantially horizontally disposed, inwardly angled elongate tucking rods 110, 112, are supported adjacent and extend inwardly through the space between legs 106a, 106b (for rod 110) and between legs 108a, 108b (for rod 112).

Referring still to FIG. 4, mounted slightly upstream in the product path from the bifurcated portions of holding elements 106, 108, and spaced laterally outwardly from rods 106, 108 are sealing units 118, 120. The sealing units illustrated include elongate upper and lower heating elements 118a, 118b, 120a, 120b, respectively, positioned above and below the path along which a product will be carried to seal side seams of a product, as will be described below.

Spaced immediately downstream from sealing units 118, 120 are severing knives 122, 124. These knives are positioned laterally outwardly from sealing units 118, 120 respectively, but laterally inwardly from the path of engaging members 64, 66.

Describing the operation of the apparatus thus far described, and referring first specifically to FIG. 1, an elongate web of flexible backsheet material 12 is drawn from roll 14, and is carried past waist elastic applicator 22 which applies waist elastic elements extending laterally of the backsheet as indicated generally at 42 in FIG. 2. A plurality of longitudinally spaced absorbent pads 26 are deposited upon backsheet 12 atop conveyor 18.

Elongate leg elastic elements, such as those indicated generally at 44 in FIG. 2 are applied substantially longitudinally to the backsheet 12. As is seen in FIG. 2, the leg elastics are disposed in a somewhat curvilinear path spaced inwardly from the outer side edges 40a, 40b of composite product 40.

An elongate web of flexible sheet material to form an inner liner 34 is drawn from roll 36 and is applied atop backsheet 12 overlying pad 26 to encase and enclose the pad and waist and leg elastics therein. The composite thus formed is carried in the direction of path 54 and over a roller indicated generally at 126 in FIG. 5.

A pair of silicone rollers, such as those indicated generally at 128, 130 in FIGS. 5 and 7 receive edge margin portions of the composite product 40 therebetween and guide the material over the pins 64b, 66b of the engaging members 64, 66 to drive the pins through edge margin portions of the backing and liner sheets. As is best seen in FIGS. 7 and 12, since the pins are angled laterally outwardly from the center of the path for the product, the natural tendency of the product to contract due to the elastic members therein will hold the product tightly on the pins of the engaging members.

Conveyor chains 74, 84 are driven by drive mechanism (not shown) at the selected speed for movement of the product through the apparatus. As is seen in FIG. 2, a first set of engaging members 64 engage opposed side edge margins of a portion of the composite product adjacent what will be considered a leading end edge of a product adjacent separation line 48. Engaging members 66 at opposite sides of the path hold opposite side edge margins of the material adjacent what is referred to herein as the trailing edge adjacent separation line 50. The conveyor chains and engaging members are sufficiently rigid and well supported that they will hold the materials in substantially stretched condition, resisting the contracting forces of the waist and leg elastic elements.

The composite 40 is carried into the region of the water jets 56 which includes a pair of water jets mounted on swing arms 56a, 56b, as is known. The arms and jets swing laterally inwardly and outwardly in preselected timed relation to form incut leg regions indicated generally at 130 at opposite side margins of the product. These incut leg regions are defined at opposite sides of each discrete product to be produced and are substantially centrally located longitudinally of the product.

The product then is carried further downstream to a final knife region 58 at which a rotary knife severs the product along separation lines 48, 50 to form a discrete product, or garment, 134A.

Figure 6:
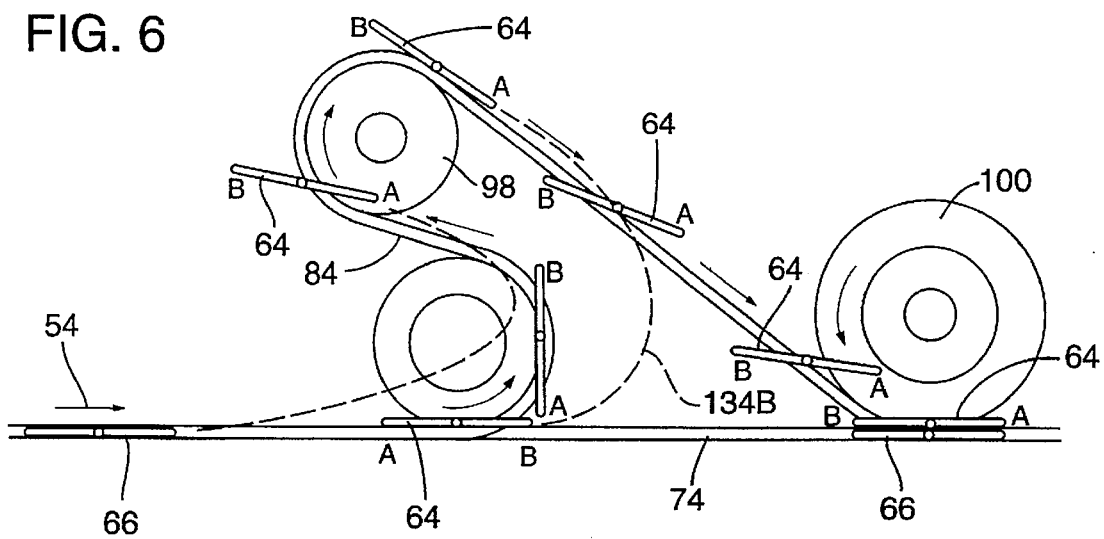
FIG. 6 is an enlarged side elevation view of a portion of the conveyor mechanism illustrated in FIG. 5.

As the conveyor chains reach the region of sprockets 96 illustrated in FIGS. 5 and 6, conveyor chains 74 continues to move in a substantially horizontal path. Conveyor chains 84 at opposite sides of the path however, carrying engaging members 64, are carried upwardly along the curvilinear path winding around sprockets 96, 98, and thence downwardly under sprocket 100.

FIG. 6 illustrates sequential positions for an engaging member 64 as it moves with its associated conveyor chain 84 about the path provided by sprockets 96, 98, and 100. In FIG. 6, opposite ends of an engaging member 64 are designated A, B, respectively. With this designation it can be seen that the engaging members 64 holding the leading edge portions of a garment 134B are inverted, or turned over, as they pass around this series of sprockets. The pivot connections 78 between engaging members 64 and their conveyor chains 84 permit this turning to occur. It has been found that this inverting action occurs naturally due to the movement of the conveyor chains, engaging members and elasticity of the product being carried. It should be recognized however, that if the elasticity of the product is insufficient to cause inversion to occur, various forms of ancillary turning mechanism, such as cams, or engaging mechanism may be used to produce the necessary action.

As is seen in FIG. 3, engaging members 64 initially are positioned a substantial distance ahead of engaging members 66 for each product as they are moved along the product path. However, the movement of conveyor chains 84 about sprockets 96, 98, 100 significantly retards the movement of engaging members 64 relative to the movement of engaging members 66 in the direction of path 54, such that engaging members 64, and the leading end portion of the garment which they carry, come into overlying registry with engaging members 66 and the trailing end portion of the product carried by members 66.

This overlying relationship of engaging members 64, 66 to bring the leading and trailing portions of the garment into registry, is illustrated in FIGS. 4, 6, 10, and 11. Engaging members 64 closely overlie engaging members 66 and due to the angularity of their teeth 64b, 66b, they continue to hold side edge margins of the end portions of the garment in a laterally stretched condition.

Referring again to FIG. 3, it will be seen that the garment 134B is folded over by the operation just described about its mid-region or central crotch region, which is free of engagement by the engaging members 64, 64. The incut leg margin regions 130 move into the space between holding rods 106, 108. The trailing end portion of the garment moves under rods 106, 108 and the leading end portion is disposed atop the rods.

Moving to FIG. 4, as the engaging members again are brought into overlying relationship, the engaging members 64, 66 are positioned laterally outwardly from rods 106, 108. This positioning is illustrated schematically in FIG. 13. Engaging members 64, 66 carried by their associated conveyor chains 74, 84 carry folded-over product 134C through sealing units 118, 120 respectively. Opposed portions of the product are contacted by heated elements 118a, 118b at one side of the product and by 120a, 120b at the opposite side of the products. What had been the leading and trailing end portions of garment 134C thus are heat sealed together at a seam region by sealing units 118, 120 as is known, and shown schematically in FIG. 14. It will be recognized that heat sealing units are used for illustrative purposes only and other methods for sealing side seams of the product may be used. This produces a garment having a continuous waist band area.

Figure 14:
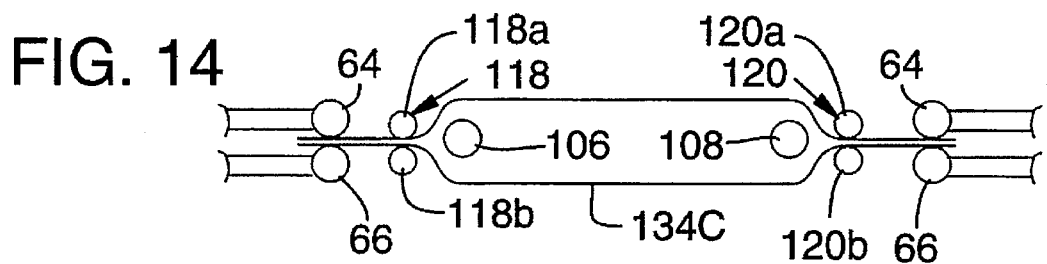
Figure 15:
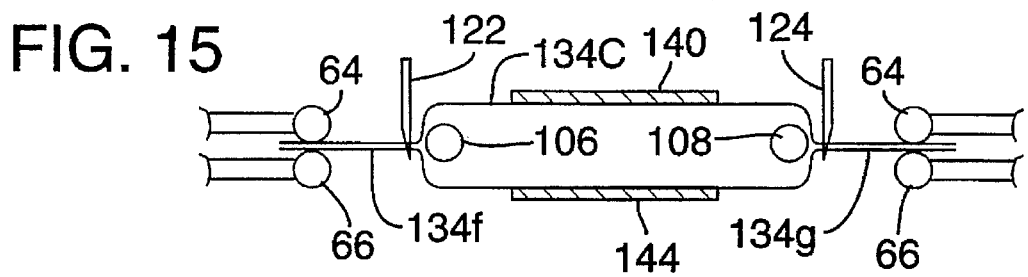

The garment 134C exiting sealing units 118, 120 is carried through severing knives 122, 124 as illustrated schematically in FIG. 14 which severs portions 134f, 134g from garment 134C, with portions 134f, 134g becoming waste to be carried away therefrom by engaging members 64, 66. At this point, the garment is captured between an upper conveyor 140, and a lower conveyor 144, shown schematically only, which will continue to move the product to the end of the assembly process.

As a product 134D moves into the region of bifurcated legs 106a, 106b, and 108a, 108b, it is spread apart vertically to produce side regions 134h and 134i adjacent opposite sides of the garment spanning the spaces between the bifurcated legs.

Figure 16:
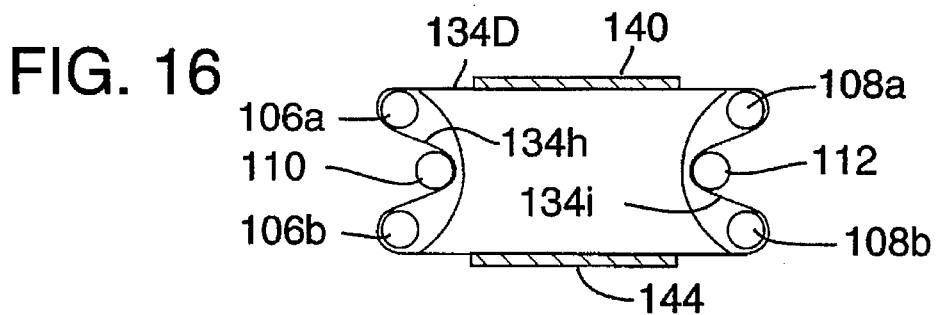
Figure 17:
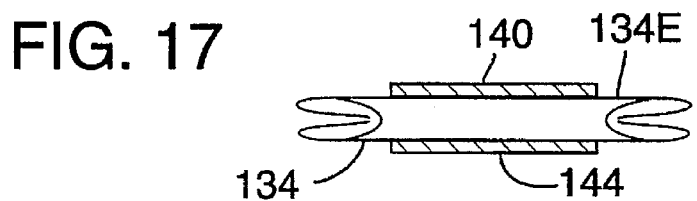

The garment is moved along the path and engaged by tucking rods 110, 112 which fold in regions of sides 134h, 134i between the bifurcated legs as illustrated in FIG. 16 and tuck the side regions into the configuration illustrated in FIG. 16. A finished garment is indicated generally at 134E in FIGS. 4 and 17 with an enclosing elasticized waistband 150, elasticized leg cuffs 130, and inwardly folded side edge margins ready to be inserted into a waiting package 152.

While a preferred embodiment of the invention has been described herein, it should be apparent to those skilled in the art that variations and modifications are possible without departing from the spirit of the invention.

I claim:

1. In an apparatus for producing an absorbent garment the improvement comprising a mechanism for joining together a first elongate web of flexible sheet material, a second elongate web of flexible sheet material, absorbent pad material interposed and encased between said first and second webs, and elastic material extending laterally and longitudinally of the sheet material to form an elongate composite, said composite having sections adapted to be separated therefrom to form discrete products each having opposed ends and opposed sides, at least four spaced apart engaging members operable to engage and hold the composite adjacent portions thereof which define opposed end regions and Opposed side region of a discrete product, each member positioned to engage the product adjacent an intersection between an end region and a side region thereof and said engaging members being spaced apart a distance to maintain the product stretched longitudinally and laterally, a conveyor comprising a pair of spaced elongate first conveyor elements disposed adjacent and extending along opposite side margins of the path for the product on which conveyor elements said engaging members are mounted to maintain selected spacing between said engaging members to maintain said product stretched both longitudinally and laterally of the product and to carry said engaging members along the path for the product at a selected speed for the product while maintaining said selected spacing therebetween, said conveyor further comprising means for driving said conveyor elements in the direction of said path, and severing mechanism operable to sever a discrete product from the composite formed, said engaging members being positioned to engage the discrete product adjacent opposed ends and sides thereof to maintain a stretched condition for the product against the urging of the elastic to contract the product as it is moved along the path after severing.

2. The apparatus of claim 1, wherein said first conveyor elements carry a first pair of opposed engaging members positioned to engage opposed side edge margins of the product adjacent a leading portion of the product as it is moved along said path, and which further comprises a second pair of conveyor elements disposed adjacent and extending along opposite side margins of the path which carry a second pair of opposed engaging members spaced longitudinally of the path from the first pair of engaging members positioned to engage opposed side margins of the product adjacent a trailing portion of the product as it is moved along the path.

3. In an apparatus for producing an absorbent garment the improvement comprising a mechanism for joining together a first elongate web of flexible sheet material, a second elongate web of flexible sheet material, absorbent pad material interposed and encased between said first and second webs, and elastic material extending laterally and longitudinally of the sheet material to form an elongate composite, said composite having sections adapted to be separated therefrom to form discrete products each having opposed ends and opposed sides, a plurality of spaced apart engaging members operable to engage and hold the composite adjacent portions thereof which define opposed end regions and opposed side region of a discrete product including at least four members each positioned to engage the product adjacent an intersection between an end region and a side region thereof and said engaging members being spaced apart a distance to maintain the product stretched longitudinally and laterally, a conveyor operable to maintain selected spacing between said engaging members to maintain said product stretched both longitudinally and laterally of the product and to carry said engaging members along the path for the product at a selected speed for the product while maintaining said selected spacing therebetween, including a pair of spaced elongate first conveyor elements disposed adjacent and extending along opposite side margins of the path which first conveyor elements carry a first pair of opposed engaging members positioned to engage opposed side edge margins of the product adjacent a leading portion of the product as it is moved along said path, and a second pair of conveyor elements disposed adjacent and extending along opposite side margins of the path which second conveyor elements carry a second pair of opposed engaging members spaced longitudinally of the path from the first pair of engaging members positioned to engage opposed side margins of the product adjacent a trailing portion of the product as it is moved along the path, said conveyor further including means for driving said conveyor elements in the direction of said path, a severing mechanism operable to sever a discrete product from the composite formed, said engaging members being positioned to engage the severed product adjacent opposed ends and sides thereof to maintain a stretched condition for the product against the urging of the elastic to contract the product as it is moved along the path, said first pair of engaging members being pivotally mounted on said first conveyor elements, and a turning mechanism operable to cause said first engaging members to pivot as they are moved along said path to fold a leading portion of the product over a trailing portion thereof.

4. The apparatus of claim 3, wherein said turning mechanism comprises a mechanism operable to retard movement of said first conveyor elements longitudinally of the path relative to said second conveyor element in the region of said turning mechanism to place the leading portion of the product in registry with said trailing portion of the product.

5. The apparatus of claim 4, which further comprises a joining mechanism downstream in said path from said turning mechanism operable to join selected regions of said leading and trailing portions of the product.

6. The apparatus of claim 5, wherein said joining mechanism is positioned laterally inwardly of the path of said engaging members whereby said selected regions are joined inwardly of the engaging members and which further comprises another severing mechanism downstream in said path from said joining mechanism operable to sever said product along lines intermediate said engaging members and said joined regions.

7. The apparatus of claim 3, wherein the paths of said first and second conveyor elements diverge in the region of said turning mechanism, said first conveyor elements are moved longitudinally of the path at a slower speed than said second conveyor elements in the region of the turning mechanism to place the leading portion in registry with the trailing portion of the product with a folded over mid-region of the product therebetween free of engagement by an engaging member, and which further comprises an elongate holding element extending longitudinally of the path positioned intermediate said diverging conveyor elements in the turning region and laterally inwardly of said engaging elements to extend through a gap at the mid-region of the folded-over product.

8. The apparatus of claim 7, which further comprises joining mechanism downstream in said path from said turning mechanism operable to join together selected portions of said leading and trailing portions held by said engaging members in regions intermediate said engaging members and said holding element.

9. The apparatus of claim 8, which further comprises another severing mechanism downstream in said path from said joining mechanism operable to sever said product along a line extending substantially longitudinally of said path intermediate said engaging members and said joined regions.

10. The apparatus of claim 9, wherein said elongate holding element has a bifurcated portion including a pair of elongate substantially parallel spaced legs operable to engage an inner side of said joined region of said product and produce spreading thereof with a portion of the product spanning the space between said legs, and which further comprises a tucking member positioned to engage and tuck a portion of said product spanning the space between said legs into a fold extending laterally inwardly of the path between said legs.

11. In an apparatus for producing an absorbent garment the improvement comprising a mechanism for joining together a first elongate web of flexible sheet material, a second elongate web of flexible sheet material, absorbent pad material interposed and encased between said first and second webs, and elastic material extending laterally and longitudinally of the sheet material to form an elongate composite, said composite having sections adapted to be separated therefrom to form discrete products each having opposed ends and opposed sides, said elastic material tending to contract the composite laterally and longitudinally, at least four spaced apart engaging members operable to engage and hold the composite adjacent portions thereof which define opposed end regions and opposed side regions of a discrete product, each member positioned to engage the product adjacent an intersection between an end region and a side region thereof and said engaging members being spaced apart a distance to maintain the product stretched longitudinally and laterally, a conveyor operable to maintain selected spacing between said engaging members to maintain said product stretched both longitudinally and laterally and to carry said engaging members along the path for the product at a selected speed while maintaining said selected spacing therebetween, said conveyor including a pair of spaced elongate first conveyor elements disposed adjacent and extending along opposite side margins of the path which first conveyor elements carry a first pair of opposed engaging members positioned to engage opposed side edge margins of the product adjacent a leading portion of the product as it is moved along said path, and a second pair of conveyor elements disposed adjacent and extending along opposite side margins of the path which second conveyor elements carry a second pair of opposed engaging members spaced longitudinally of the path from the first pair of engaging members positioned to engage opposed side margins of the product adjacent a trailing portion of the product as it is moved along the path, said conveyor further including means for driving said conveyor elements in the direction of said path, and a turning mechanism operable to retard movement of the first conveyor elements longitudinally of the path relative to the second conveyor elements to place the leading portion of the product in registry with the trailing portion of the product.

12. In an apparatus for producing an absorbent garment, the improvement comprising a mechanism for joining together a first elongate web of flexible sheet material, a second elongate web of flexible sheet material, absorbent pad material interposed and encased between said first and second webs, and elastic material extending laterally and longitudinally of the sheet material to form an elongate composite, said composite having sections adapted to be separated therefrom to form discrete products each having opposed ends and opposed sides, at least four spaced-apart engaging members operable to engage and hold the composite adjacent portions thereof which define opposed end regions and opposed side regions of a discrete product, each member positioned to engage the product adjacent an intersection between an end region and a side region thereof, and said engaging members being spaced apart a distance to maintain the product stretched longitudinally and laterally, a conveyor comprising a pair of spaced elongate first conveyor elements disposed adjacent and extending along opposite side margins of the path for the product on which conveyor elements a first pair of opposed engaging members are positioned to engage opposed side edge margins of the product adjacent a leading portion of the product as it is moved along said path and a second pair of conveyor elements disposed adjacent and extending along opposite side margins of the path which carry a second pair of opposed engaging members spaced longitudinally of the path from the first pair of engaging members positioned to engage opposed side margins of the product adjacent a trailing portion of the product as it is moved along the path, said engaging members being mounted to maintain selected spacing between said engaging members to maintain said product stretched both longitudinally and laterally of the product and to carry said engaging members along the path for the product at a selected speed for the product, while maintaining said selected spacing therebetween, said conveyor further comprising means for driving said conveyor elements in the direction of said path, and a severing mechanism operable to sever a discrete product from the composite formed and said engaging members are positioned to engage the severed product adjacent opposed ends and sides thereof to maintain a stretched condition for the product against the urging of the elastic to contract the product as it is moved along the path after severing.

\* \* \* \* \*